United States Patent [19]

Jäger

[11] 4,000,173
[45] Dec. 28, 1976

[54] 3-ARYL-2-HALOTHIOPROPIONIC ACID S-ESTERS

[75] Inventors: Gerhard Jäger, Wuppertal; Robert Rudolf Schmidt, Cologne, both of Germany

[73] Assignee: Bayer Aktiengesellschaft, Leverkusen, Germany

[22] Filed: May 2, 1972

[21] Appl. No.: 249,575

[30] Foreign Application Priority Data

May 6, 1971 Germany ............ 2122309

[52] U.S. Cl. ............ 260/455 R; 260/455 B; 260/502.6; 71/100
[51] Int. Cl.$^2$ ............ C07C 153/07
[58] Field of Search ............ 260/455 R, 455 B

[56] References Cited
UNITED STATES PATENTS 3,696,726  7/1972  Lewis ............ 260/455 R

FOREIGN PATENTS OR APPLICATIONS 679,576  7/1966  Belgium ............ 260/455 R

OTHER PUBLICATIONS

Chem. Abstracts vol. 44 2916–2917 1950.
Chem. Abstracts vol. 60 10492G 1964.
Chem. Abstracts vol. 56 5858i 1962.
Chem. Abstracts vol. 50 7744h 1956.

*Primary Examiner*—Lewis Gotts
*Assistant Examiner*—D. R. Phillips
*Attorney, Agent, or Firm*—Burgess, Dinklage & Sprung

[57] ABSTRACT

Novel 3-aryl-2-halothiopropionic acid compounds of the formula

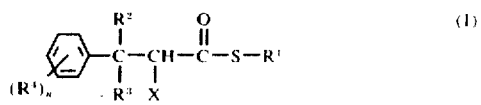

wherein
X is chlorine or bromine,
$R^1$ is hydrogen, a salt-forming cation, an aliphatic radical or a substituted aliphatic radical wherein the substituent is halogen, haloalkyl, hydroxy, alkoxy, alkoxy-carbonyl or aryl,
$R^2$ is hydrogen, halogen or alkyl
$R^3$ is hydrogen or alkyl
$n$ is an integer from 0 to 3; and
$R^4$ is halogen, alkyl, haloalkyl or nitro and wherein the radical $R^4$ when $n$ is 2 or 3, may be the same or different, are outstandingly effective herbicides, exhibiting particularly selective action.

21 Claims, No Drawings

3-ARYL-2-HALOTHIOPROPIONIC ACID S-ESTERS

The present invention relates to certain new 3-aryl-2-halothiopropionic acid compounds, to compositions containing them and to their use as herbicides.

It is already known that phenylcarboxylic acid derivatives, in particular 3-(p-chlorophenyl)-2-chloropropionic acid methyl ester, exhibit selectively herbicidal properties (see U.S. Pat. Specification No. 3,427,646; Belgian Pat. Specification No. 679,576; L. Eue, Zeitschrift fur Pflanzenkrankheiten und Pflanzenschutz, Sonderheft (Special Issue) IV, (1968), pages 211-214). These compounds are well suited for the control of wild oats in cereals, maize, beets, beans, peas and carrots.

However, their herbicidal effectiveness, in particular that of 3-(p-chlorophenyl)-2-chloropropionic acid methyl ester, against wild oats, especially in the case of low applied amounts and applied concentrations, is not always adequate. It frequently happens, for instance, that incompletely killed wild oat plants grow through again and form caryopses capable of multiplying (see W. Kampe, Mededelingen van de Rijksfakulteit Landbouwwetenschappen te Gent XXXXIV, 3, pages 973-989, (1969).

The present invention provides, as new compounds, 3-aryl-2-halothiopropionic acid derivatives of the formula

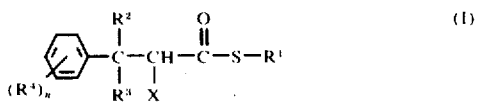

in which

X is chlorine or bromine, $R^1$ is hydrogen, a salt-forming cation or an aliphatic radical of up to about 12 carbon atoms, e.g., alkyl, alkenyl, alkynyl or cycloalkyl, which radical may optionally be carrying one or more substituents selected from halogen, haloalkyl (1-10 carbon atoms) hydroxy, alkoxy (1-10 carbon atoms) alkoxycarbonyl (1-10 carbon atoms) and aryl (1-10 carbon atoms)

$R^2$ is hydrogen, halogen or alkyl (1-10 carbon atoms)

$R^3$ is hydrogen or alkyl (1-10 carbon atoms) n is 0, 1, 2 or 3, and $R^4$ is halogen, alkyl (1-10 carbon atoms), haloalkyl (1-10 carbon atoms) or nitro, the radicals $R^4$ being identical or different when n is 2 or 3.

In formula (I) it is preferred that X be chlorine; that $R^1$ be hydrogen, ammonium, alkylammonium with 1 to 4 carbon atoms in each alkyl radical, an alkali metal ion, especially a sodium or potassium ion, straight-chain or branched alkyl with 1 to 10 carbon atoms, straight-chain or branched alkenyl or alkynyl with, in either case, 3 to 5 carbon atoms or cycloalkyl with 3 to 7 carbon atoms, the four last-mentioned radicals optionally carrying one or more substituents selected from fluorine, chlorine, bromine, hydroxyl, alkoxy with 1 to 4 carbon atoms, alkoxycarbonyl with 1 to 3 carbon atoms in the alkyl moiety or phenyl; that $R^2$ should be hydrogen, chlorine or methyl; that $R^3$ be hydrogen or methyl; that n should be 0, 1 or 2; and that the $R^4$ or each $R^4$ (if n ≥ 2) be flourine, chlorine, bromine, nitro, straight-chain or branched alkyl with 1 to 4 carbon atoms or haloalkyl with 1 to 3 carbon atoms and 1 to 3 halogen atoms, especially fluorine or chlorine.

The compound of the formula (I) above exhibit very good herbicidal, especially selectively herbicidal, properties.

Surprisingly, the 3-aryl-2-halothiopropionic acid derivatives of the formula (I) show a considerably higher selectively herbicidal activity than the phenylcarboxylic acids known from the prior art (especially 3-(p-chlorophenyl)-2-chloropropionic acid methyl ester) which are the chemically closest active compounds of the same type of activity. The compounds according to this invention therefore represent a valuable enrichment of the art.

The present invention also provides a process for the preparation of a 3-aryl-2-halothiopropionic acid derivative of the formula (I) in which a 3-aryl-2-halopropionyl halide of the general formula

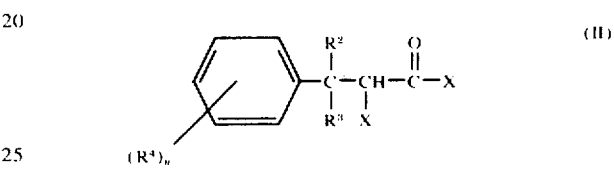

in which

X, $R^2$, $R^3$, $R^4$ and n have the meanings stated above for formula (I), the X's being identical or different, is reacted with a hydrogen sulfide compound of the general formula

in which $R^1$ has the meaning stated above for formula (I) optionally in the presence of an acid-binding agent and optionally in the presence of an inert solvent.

If 3-(p-chlorophenyl)-2-chloropropionyl chloride and n-propylmercaptan are used as the starting materials, the reaction course can be represented by the following equation:

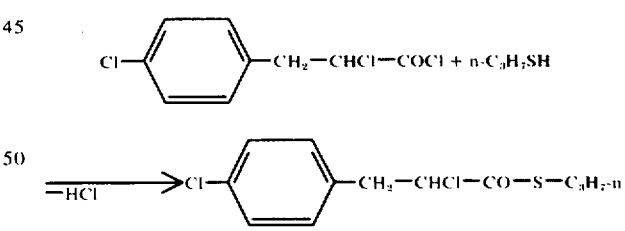

A number of the 3-aryl-2-halopropionyl halides of the formula (II) used as starting materials are known (see U.S. Pat. Specification No. 3,472,646). The acid halides of the formula (II) that have not been hitherto described in the literature can be prepared by reacting 3-aryl-1,1-dihalopropenes-(1) of the general formula

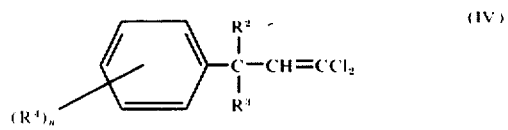

in which $R^2$ stands for alkyl or halogen,
$R^3$ stands for alkyl or hydrogen, and
$R^4$ and n have the meanings stated above for formula (I) with chlorine and formic acid (see Izvest. Akad. Nauk. SSSR, Otdel. Khim. Nauk. 1959, 826–830, reported in C.A. 54, 1333 (1960), and the preparative Examples herein). The 3-aryl-1,1-dihalopropenes-(1) of the formula (IV) are themselves known or their synthesis route is known (see U.S. Pat. Specification No. 2,894,995; Journal of American Chemical Society 75, 6216–6217 (1953)).

As examples of the 3-aryl-2-halopropionyl chlorides of the formula (II) that can be used according to this invention, there may be mentioned:
3-phenyl-2-chloropropionyl chloride,
3-phenyl-2-bromo-propionyl chloride,
3(2-chlorophenyl)-2-chloro-propionyl chloride,
3-(3-chlorophenyl)-2-chloro-propionyl chloride,
3-(4-chlorophenyl)-2-chloro-propional chloride,
3-(4-bromophenyl)-2-chloro-propionyl chloride,
3-(4-fluorophenyl)-2-chloro-propionyl chloride,
3-(4-bromophenyl)-2-bromo-propionyl chloride,
3-(2,4-dichlorophenyl)-2-chloro-propionyl chloride,
3-(3,4-dichlorophenyl)-2-chloro-propionyl chloride,
3-(2,6-dichlorophenyl)-2-chloro-propionyl chloride,
3-(3,4-dichlorophenyl)-2-bromo-propionyl chloride,
3-(4-methylphenyl)-2-chloro-propionyl chloride,
3-(4-nitrophenyl)-2-chloro-propionyl chloride,
3-(3-nitrophenyl)-2-chloro-propionyl chloride,
3-(3-trifluoromethylphenyl)-2-chloro-propionyl chloride,
3-(4-chloro-3-nitrophenyl)-2-chloro-propionyl chloride,
3-phenyl-3-bromo-2-chloro-propionyl chloride,
3-phenyl-3-methyl-2-chloro-propionyl chloride,
3-phenyl-3,3-dimethyl-2-chloro-propionyl chloride, and
3-(4-bromophenyl)-3-methyl-2-bromo-propionyl chloride.

The hydrogen sulfide compounds (III) used as starting materials are generally known. As examples thereof, the following compounds may be mentioned:
sodium hydrogen sulfide,
ammonium hydrogen sulfide,
methyl mercaptan,
ethylmercaptan,
n-propylmercaptan,
isopropylmercaptan,
n-butylmercaptan,
isobutylmercaptan,
tertiary butylmercaptan,
hexylmercaptan,
octylmercaptan,
dodecylmercaptan,
propargylmercaptan,
3,3-dimethyl-3-mercapto-propene-(1),
3,3-dimethyl-3-mercapto-propyne-(1),
benzylmercaptan,
3-chloro-1-mercapto-butene-(1), and
mercaptoacetic acid ethyl ester.

As diluents in the process according to this invention, all inert organic solvents are suitable, especially hydrocarbons, such as benzine, benzene, toluene or xylene, and halogenated hydrocarbons, such as dichloromethane, chloroform, tetrachloromethane, chlorobenzene or dichlorobenzene.

As the acid-binding agent any customary acid-acceptor can be used; the preferred acid-acceptor are alkali metal hydroxides, such as sodium hydroxide and potassium hydroxide; alkaline earth metal hydroxides, such as barium hydroxide; alkali metal carbonates, such as sodium carbonate; alkaline earth metal carbonates, such as calcium carbonate and barium carbonate, and tertiary organic bases, such as triethylamine and pyridine. Particularly suitable are sodium carbonate, potassium carbonate, triethylamine and pyridine.

The reaction temperatures can be varied within a fairly wide range. In general, the work is carried out at from 0° C to 150° C, preferably from 20° C to 80° C.

When carrying out the process according to the invention, for 1 mole or 3-aryl-2-halopropionyl chloride of the formula (II) there are advantageously used 1 mole of hydrogen sulfide compound of the formula (III) and 1 mole of acid-binder. Minor deviation from the stoichiometric proportions results in no substantial improvement of yield.

To isolate the compounds of the formula (I) obtainable according to the invention, the reaction solution is filtered off from the halide formed as a by-product and the filtrate is washed thoroughly with an alkali metal carbonate solution. From the well-dried organic phase the compounds of the formula (I) are obtained by distillation under reduced pressure.

The process of this invention is illustrated in and by the following preparative Examples.

EXAMPLE 1

Preparation of
3-(2,6-dichlorophenyl)-2-chloro-thiopropionic acid
S-isopropyl ester

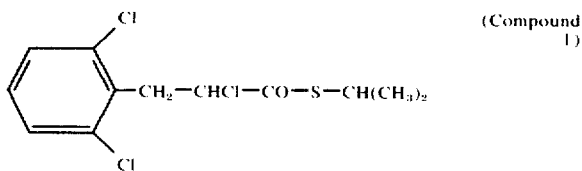

(Compound 1)

To a solution of 20 g. (0.0735 mole) of 3-(2,6-dichlorophenyl)-2-chloropropionyl chloride in 150 ml. of anhydrous benzene there were added dropwise, within 15 minutes, 6.4 g (0.0735 mole) of isopropylmercaptan and 7.5 g (0.0735 mole) triethylamine which beforehand were both dissolved together in 50 ml. of anhydrous benzene. Vigorous stirring was effected during this dropwise addition; the temperature rose to 60° C during this time. The reaction mixture was subsequently left at room temperature for half an hour, with stirring.

Thereafter, filtration from the precipitated triethylammonium chloride was effected; the filtrate was washed with dilute sodium carbonate solution and water and dried over anhydrous sodium sulfate. After the solvent had been distilled off, distillation under reduced pressure was effected and 18.8g (82 percent of the theory) of 3-(2,6-dichlorophenyl)-2-chloro-thiopropionic acid S-ispropyl ester of the boiling point 154°–156° C/0.65 mm Hg were obtained.

The 3-(2,6-dichlorophenyl)-2-chloropropionyl chloride used as the starting material was prepared as follows:

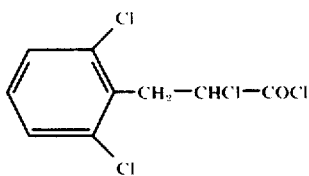

(1a)

To a solution of 126.7g (0.5 mole) of 3-(2,6-dichlorophenyl)-2-chloropropionic acid in 400 ml. of anhydrous benzene there were added 50 ml. of thionyl chloride and 0.5 ml. of dimethyl formamide and heating to the boil was effected until the cessation of evolution of hydrogen chloride (approximately 4 hours). Subsequently, the solvent and the excess thionyl chloride were removed by distillation at normal pressure. The residue was distilled under reduced pressure.

There were obtained 122g (90 percent of the theory) of 3-(2,6-dichlorophenyl)-2-chloropropionic acid chloride of the boiling point 113°–115° C/0.5 mm Hg.

EXAMPLE 2

Preparation of 3-(4-chlorophenyl)-2-chloro-thio-propionic acid S-n-propyl ester.

(Compound 2)

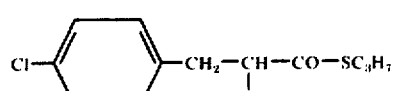

To a solution of 47.4g (0.2 mole) of 3-(4-chlorophenyl)-2-chloropropionyl chloride in 150 ml. of anhydrous benzene there were added dropwise during a quarter of an hour, with vigorous stirring, 15.2g (0.2 mole) of propylmercaptan and 20.2g (0.2 mole) of triethylamine, both dissolved in 100 ml of anhydrous benzene. The temperature rose to approximately 60° C.

After cooling, further stirring was effected for half an hour at room temperature; thereafter filtration from the precipitated triethylammonium chloride was effected and the filtrate was purified by treatment with aqueous sodium carbonate solution and water. The organic phase was dried over sodium sulfate. After the solvent had been distilled off, there were obtained by distillation under reduced pressure 46.2g (83.5 percent of the theory) of 3-(4-chlorophenyl)-2-chloro-thiopropionic acid S-n-propyl ester of the boiling point 140° C/0.4 mm Hg.

In a manner analogous to that above, the compounds listed in the following Table can be prepared:

Table (I)

| Compound No. | $R^1$ | X | $R^2$ | $R^3$ | $R^4$ | n | Refractive index or Boiling point °C/mm Hg |
|---|---|---|---|---|---|---|---|
| 3 | $-CH_3$ | Cl | H | H | 4-Cl | 1 | 123–125/0.2 |
| 4 | $-C_2H_5$ | Cl | H | H | 4-Cl | 1 | 129–130/0.2 |
| 5 | $-CH(CH_3)_2$ | Cl | H | H | 4-Cl | 1 | 136/0.8 |
| 6 | $-C_4H_9$ | Cl | H | H | 4-Cl | 1 | 175–178/1.5 |
| 7 | $-CH(CH_3)-C_2H_5$ | Cl | H | H | 4-Cl | 1 | 143–145/0.4 |
| 8 | $-C(CH_3)_3$ | Cl | H | H | 4-Cl | 1 | 131–133/0.5 |
| 9 | $-CH_2-\langle\text{phenyl}\rangle$ | Cl | H | H | 4-Cl | 1 | 194–195/0.5 |
| 10 | $-CH_2-CO-OC_2H_5$ | Cl | H | H | 4-Cl | 1 | $n_D^{25} = 1.5495$ |
| 11 | $-C_3H_7$ | Cl | H | H | 2-Cl | 1 | 132–134/0.1 |
| 12 | $-CH(CH_3)_2$ | Cl | H | H | 2-Cl | 1 | 148–150/0.7 |
| 13 | $-C_4H_9$ | Cl | H | H | 2-Cl | 1 | 143–145/0.2 |
| 14 | $-CH(CH_3)C_2H_5$ | Cl | H | H | 2-Cl | 1 | 140–142/0.3 |
| 15 | $-C(CH_3)_3$ | Cl | H | H | 2-Cl | 1 | 138–140/0.4 |
| 16 | $-C_3H_7$ | Cl | H | H | 2,6-Cl | 2 | 158–160/0.45 |
| 17 | $-CH(CH_3)-C_2H_5$ | Cl | H | H | 2,6-Cl | 2 | 159–161/0.4 |
| 18 | $-C_4H_9$ | Cl | H | H | 2,6-Cl | 2 | 164–166/0.3 |
| 19 | $-C(CH_3)_3$ | Cl | H | H | 2,6-Cl | 2 | 158–160/0.5 |
| 20 | $C_3H_7$ | Cl | H | H | 3,4-Cl | 2 | 154–156/0.25 |
| 21 | $-CH(CH_3)_2$ | Cl | H | H | 3,4-Cl | 2 | 148–150/0.25 |
| 22 | $C_4H_9$ | Cl | H | H | 3,4-Cl | 2 | 163–165/0.25 |
| 23 | $-CH(CH_3)-C_2H_5$ | Cl | H | H | 3,4-Cl | 2 | 161–163/0.5 |
| 24 | $-C(CH_3)_3$ | Cl | H | H | 3,4-Cl | 2 | 154–155/0.5 |
| 25 | $C_3H_7$ | Cl | H | H | 3-CF_3 | 1 | 111/0.55 |
| 26 | $C_3H_7$ | Cl | H | Br | 4-Cl | 1 | |
| 27 | $C_3H_7$ | Cl | $CH_3$ | $CH_3$ | 4-Cl | 1 | |
| 28 | $-CH(CH_3)_2$ | Cl | H | H | 3-CF_3 | 1 | 150/1.1 |
| 29 | $-C_3H_7$ | Cl | $CH_3$ | H | 4-Cl | 1 | 142/0.6 |
| 30 | $-C_3H_7$ | Cl | H | H | 2,6-Cl, 4-NO_2 | 3 | $n_D^{20} = 1.5848$ |

Preparation of 2-chloro-3-(4'-chlorophenyl)-propionyl chloride

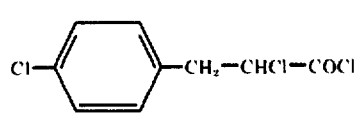

(2a)

221.5g (1 mole) of 1,1-dichloro-3-(4-chlorophenyl)-propene were mixed with 2500 ml. of formic acid that contained 18g (1.0 mole) of water. The mixture was brought to 70° C (internal temperature), then chlorine was introduced.

After about 10 minutes, a vigorous evolution of hydrogen chloride set in. Within half an hour a clear, almost colorless solution was obtained. The internal temperature rose to 80°-82° C. Chlorine was now introduced until the solution was yellow-colored (about 10–15 minutes). Subsequently, heating to the boil was effected for half an hour and thereafter the formic acid was distilled off; 2-chloro-3-(4'-chlorophenyl)-propionyl chloride remained behind.

The active compounds according to the invention influence plant growth very strongly, but in a variable manner, so that they can be used particularly as selective herbicides. If, however, the active compounds according to the invention are used in very high applied amounts they have a total herbicidal effect.

By "weeds" in the widest sense are meant all plants which grow in places where they are not desired.

The active compounds of this invention can be used, for example, in the case of the following plants: dicotyledons, such as mustard (*Sinapsis*), cress (*Lepidium*), cleavers (*Galium*), chickweed (*Stellaria*), chamomile (*Matricaria*), gallant soldier (*Galinsoga*), goosefoot (*Chenopodium*), annual nettle (*Urtica*), groundsel (*Senecio*), cotton (*Gossypium*), beets (*Beta*), carrots (*Daucus*), beans (*Phaseolus*), potatoes *Solanum*) and coffee (*Coffea*); and monocotyledons, such as timothy (*Phleum*), bluegrass (*Poa*), fescue (*Festuca*), goosegrass (*Eleusine*), foxtail (*Setaria*), ryegrass (*Lolium*), cheat (*Bromus*), barnyard grass (*Echinochloa*), maize (*Zea*), rice (*Oryza*), oats (*Avena*), barley (*Hordeum*), wheat (*Triticum*), millet (*Panicum*) and sugar cane (*Saccharum*).

The active compounds according to the invention show a very good activity against oat species without damaging the cultivated plants. They can therefore be used as selective herbicides, above all for the control of oat species, particularly wild oats (*Avena fatua*) in agricultural cultivations, especially in cereals, such as wheat, barley, rye and maize as well as in beans, peas and beets. Cultivated oats (*Avena sativa*) can be controlled in other cultivations or at places where they grow undesirably, for example on adjoining ways. With the use of very high applied amounts the active compounds can be used for total control of weeds, for example at waysides, playgrounds, ways and sports grounds.

The active compounds according to the present invention can be converted into the usual formulations, such as solutions, emulsions, suspensions, powders, pastes and granulates. These may be produced in known manner, for example by mixing the active compounds with extenders, that is, liquid or solid or liquified gaseous diluents or carrers, optionally with the use of surface-active agents, that is, emulsifying agents and/or dispersing agents. In the case of the use of water as an extender, organic solvents can, for example, also be used as auxiliary solvents.

As liquid diluents or carriers, there are preferably used aromatic hydrocarbons, such as xylenes, toluene, benzene or alkyl naphthalenes, chlorinated aromatic or aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethyl formamide, dimethyl sulfoxide or acetonitrile, as well as water.

By liquefied gaseous diluents or carriers are meant liquids which would be gaseous at normal temperatures and pressures, for example aerosol propellants, such as halogenated hydrocarbons, for example freon.

As solid diluents or carriers, there are preferably used ground natural minerals, such as kaolins, clays, talc, chalk, quartz, attapulgite, montmorillonite or diatomaceous earth, or ground synthetic minerals, such as highly-dispersed silicic acid, alumina or silicates.

Preferred examples of emulsifying agents include nonionic and anionic emulsifiers, such as polyoxyethylene-fatty acid esters, polyoxyethylene-fatty alcohol ethers, for example alkylarylpolyglycol ethers, alkyl sulfonates, alkyl sulfates and aryl sulfonates; and preferred examples of dispersing agents include lignin, sulfite waste liquors and methyl cellulose.

The active compounds according to the invention may be present in the formulations in admixture with other active compounds.

The formulations contain, in general, from 0.1 to 95, preferably from 0.5 to 90, percent by weight of active compound.

The active compounds may be applied as such, in the form of their formulations or in the application forms prepared therefrom, such as ready-to-use solutions, emulsions, suspensions, powders, pastes and granulates. Application may take place in any usual manner, for example by squirting, watering, dusting or scattering.

Application is possible according to both the post-emergence process and the pre-emergence process; it is effected preferably after the emergence of the plants.

In the case of use after emergence, the concentration of active compound can be varied within fairly wide ranges. In general, concentrations of active compound of from 0.01 to 1.0, preferably from 0.05 to 0.5, percent by weight are used.

In the case of application before emergence, it is also possible to use applied amounts that are within a fairly wide range. In general, applied amounts, referred to the active compound, of 0.1 to 20 kg/hectare, preferably 0.5 to 15 kg/hectare, are used.

The active compounds according to the invention also possess an insecticidal and acaricidal effectiveness. They are, on the other hand, very well tolerated by warm-blooded animals.

The present invention also provides a herbicidal composition containing as active ingredient a compound of the present invention in admixture with a solid or liquified gaseous diluent or carrier or in admixture with a liquid diluent or carrier containing a surface-active agent.

The present invention also provides a method of combating weeds which comprises applying to the weeds or a weed habitat a compound of the present invention alone or in the form of a composition containing as active ingredient a compound of the present invention in admixture with a diluent or carrier.

The present invention further provides crops protected from damage by weeds by being grown in areas in which immediately prior to and/or during the time of the growing a compound of the present invention was applied alone or in admixture with a diluent or carrier.

It will be seen that the usual methods of providing a harvested crop may be improved by the present invention.

The herbicidal effectiveness of the compounds of this invention is illustrated in and by the following test Examples.

The active compounds, the concentrations of the active compound and the results can be seen from the following Table:

Table A

| | Post-emergence test Degree of damage in %, 10 days after application of the following active compounds | | | | | | |
|---|---|---|---|---|---|---|---|
| Active compound | Concentration of active compound % | Wild oats | Oats | Mustard | Beets | Wheat | Barley |
| Cl—⟨C₆H₄⟩—CH₂—CHCl—COOCH₃ (known) | 0.2 | 94 | 94 | 60 | 10 | 0 | 15 |
| | 0.1 | 90 | 80 | 40 | 0 | 0 | 0 |
| Cl—⟨C₆H₄⟩—CH₂—CH(Cl)—CO—SC₂H₅ (Compound 6) | 0.2 | 100 | 100 | 100 | 0 | 10 | 15 |
| | 0.1 | 96 | 96 | 70 | 0 | 0 | 0 |
| Cl—⟨C₆H₄⟩—CH₂—CH(Cl)—CO—SC₃H₇ (Compound 2) | 0.2 | 100 | 100 | 100 | 5 | 10 | 10 |
| | 0.1 | 94 | 96 | 65 | 0 | 0 | 0 |
| Cl—⟨C₆H₄⟩—CH₂—CH(Cl)—CO—S—CH(CH₃)₂ (Compound 5) | 0.2 | 100 | 100 | 85 | 5 | 10 | 10 |
| | 0.1 | 96 | 94 | 60 | 0 | 0 | 0 |
| Cl—⟨C₆H₄⟩—CH₂—CH(Cl)—CO—S—CH(C₂H₅)(CH₃) (Compound 7) | 0.2 | 100 | 98 | 94 | 0 | 0 | 5 |
| | 0.1 | 90 | 94 | 60 | 0 | 0 | 0 |
| Cl—⟨C₆H₄⟩—CH₂—CH(Cl)—CO—S—CH₂—⟨C₆H₅⟩ (Compound 9) | 0.2 | 98 | 96 | 80 | 0 | 0 | 0 |
| | 0.1 | 90 | 85 | 60 | 0 | 0 | 0 |
| Cl—⟨C₆H₄⟩—CH₂—CH(Cl)—CO—SCH₃ (Compound 3) | 0.2 | 100 | 100 | 100 | 10 | 0 | 15 |
| | 0.1 | 98 | 98 | 80 | 0 | 0 | 5 |

EXAMPLE A

Post-emergence test

| Post-emergence test | |
|---|---|
| Solvent: | 5 parts by weight acetone |
| Emulsifier: | 1 part by weight alkylarylpolyglycol ether |

To produce a suitable preparation of active compound, 1 part by weight of active compound was mixed with the stated amount of solvent, the stated amount of emulsifier was added and the concentrate was then diluted with water to the desired concentration.

Test plants which had a height of about 5 to 15 cm were sprayed with the preparation of the active compound until just dew moist. After three weeks, the degree of damage to the plants was determined and designated by the values 0 to 100 which have the following meaning:

0: no damage (as in control test)
50: 50 percent damage or growth inhibition
100: 100 percent damage, that is plant totally dead.

It will be understood that the specification and examples are illustrative but not limitative of the present invention and that other embodiments within the spirit and scope of the invention will suggest themselves to those skilled in the art.

What is claimed is:

1. 3-Aryl-2-halothiopropionic acid compounds of the formula

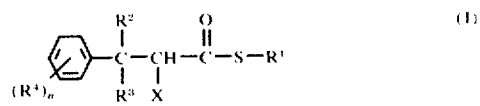

wherein

X is chlorine or bromine,

R¹ is an aliphatic radical of up to 12 carbon atoms, or a substituted aliphatic radical of up to 12 carbon atoms wherein the substituent is halogen, haloalkyl of from 1 to 10 carbon atoms, hydroxy, alkoxy of from 1 to 10 carbon atoms, alkoxycarbonyl of from 1 to 10 carbon atoms or aryl of up to 10 carbon atoms, R² is hydrogen, halogen or alkyl of from 1 to 10 carbon atoms, R³ is hydrogen or alkyl of from 1 to 10 carbon atoms,
n is an integer from 0 to 3; and
R⁴ is halogen, alkyl of from 1 to 10 carbon atoms, haloalkyl of from 1 to 10 carbon atoms or nitro and wherein the radical R⁴, when n is 2 or 3, may be the same or different.

2. Compound as claimed in claim 1 wherein said aliphatic radical defining R¹ is alkyl, alkenyl, alkynyl or cycloalkyl.

3. Compound as claimed in claim 1 wherein R¹ is alkyl of from 1 to 10 carbon atoms.

4. Compound as claimed in claim 1 wherein R¹ is alkenyl or alkynyl of from 3 to 5 carbon atoms.

5. Compound as claimed in claim 1 wherein R¹ is cycloalkyl of from 3 to 7 carbon atoms.

6. Compound as claimed in claim 1 wherein R¹ is a substituted aliphatic radical wherein the aliphatic radical is alkyl of from 1 to 10 carbon atoms, alkenyl or alkynyl of from 3 to 5 carbon atoms, or cycloalkyl of from 3 to 7 carbon atoms, and the substituent is fluorine, chlorine, bromine or hydroxyl, alkoxy of from 1 to 4 carbon atoms, alkoxycarbonyl of from 1 to 3 carbon atoms in the alkyl moiety or phenyl.

7. Compound as claimed in claim 1 wherein X is chlorine.

8. Compound as claimed in claim 1 wherein R² is hydrogen, chlorine or methyl.

9. Compound as claimed in claim 1 wherein R³ is hydrogen or methyl.

10. Compound as claimed in claim 1 wherein n is 0, 1 or 2.

11. Compound as claimed in claim 1 wherein n is 1 to 3 and R⁴ is individually selected from the group consisting of fluorine, chlorine, bromine, nitroalkyl of from 1 to 4 carbon atoms, or haloalkyl of from 1 to 3 carbon atoms.

12. Compound as claimed in claim 1 wherein said compound is 3-(2,6-dichlorophenyl)-2-chloro-thiopropionic acid S-isopropyl ester.

13. Compound as claimed in claim 1 wherein said compound is 3-(4-chlorophenyl)-2-chloro-thiopropionic acid S-n-propyl ester.

14. Compound as claimed in claim 1 wherein said compound is 3-(4-chlorophenyl)-2-chloro-thiopropionic acid S-methyl ester.

15. Compound as claimed in claim 1 wherein said compound is 3-(4-chlorophenyl)-2-chloro-thiopropionic acid S-benzyl ester.

16. Compound as claimed in claim 1 wherein said compound is 3-(4-chlorophenyl)-2-chloro-thiopropionic acid S-ethoxy-carbonyl methyl ester.

17. Compound as claimed in claim 1 wherein said compound is 3-(4-chlorophenyl)-3,3-dimethyl-2-chloro-thiopropionic acid S-n-propyl ester.

18. Compound as claimed in claim 1 wherein said compound is 3-(4-chlorophenyl)-3-methyl-2chloro-thiopropionic acid S-n-propyl ester.

19. Compound as claimed in claim 1 wherein said compound is 34-chlorophenyl)-2-chlorothiopropionic acid S-isopropyl ester.

20. Compound as claimed in claim 1 wherein said compound is 3-(4-chlorophenyl)-2-chlorothiopropionic pionic acid S-n-butyl-ester.

21. Compound as claimed in claim 1 wherein said compound is 3-(4-chlorophenyl)-2-chlorothiopropionic acid S-sec.-butyl ester.

* * * * *